(12) United States Patent
Huang

(10) Patent No.: US 6,372,785 B1
(45) Date of Patent: Apr. 16, 2002

(54) SYNTHESIS OF 1,8-DICHLORO-ANTHRACENE ANALOGUES AND PHARMACEUTICAL COMPOSITIONS BASED THEREON

(75) Inventor: Hsu-Shan Huang, Taipei (TW)

(73) Assignee: Keith Chan, President GloboAsia, LLC, Hanover, MD (US)

( * ) Notice: Subject to any disclaimer, the term of this patent is extended or adjusted under 35 U.S.C. 154(b) by 0 days.

(21) Appl. No.: 09/563,915

(22) Filed: May 4, 2000

(51) Int. Cl.$^7$ ............................................... A01N 37/10
(52) U.S. Cl. ........................ 514/532; 514/552; 514/886; 514/914; 552/208; 560/8; 560/129
(58) Field of Search .................. 560/8, 129; 552/208; 514/886, 914, 532, 552

(56) References Cited

U.S. PATENT DOCUMENTS 4,719,049 A * 1/1988 Blair
4,803,221 A * 2/1989 Blair

OTHER PUBLICATIONS

Barnett, W Chem, vol. 62, 1929, pp. 3069.*

Zee–Cheng; Robert K.Y.; Antineoplastic Agents. Structure–Activity Relationship Study Bis(substituted aminoalkylamino)anthraquinones; J. Med. Chem, vol. 21, p. 291–294 (1978).

Zee–Cheng, Robert K. Y.; Structure–Activity Relationship Study of Anthraquinones: 1,4–Dihydroxy–5,8–bis [(2–(2–hydroxyethoxy)ethyl]amino – 9,10–anthracenedione, . . . J. Pharm. Sci., vol. 71, p. 708–709 (1982).

Murdock, K. C.; Antitumore Agents. 1. 1,4–Bis[(aminoalkyl)amino]–9,10–anthracenediones; J. Med. Chem.; vol. 22, p. 1024–1030 (1979).

(List continued on next page.)

*Primary Examiner*—Paul J. Killos
*Assistant Examiner*—Héctor M Reyes
(74) *Attorney, Agent, or Firm*—Fei-Fei Chao; Venable, Baetjer, Howard & Civiletti, LLP

(57) ABSTRACT

The invention provides novel anthracene compounds useful in the treatment of allergic, inflammatory, and tumor conditions and therapeutic compositions containing such compounds or their pharmaceutically acceptable salts. The compounds of the invention are novel 1,8-dichloro-anthracene derivatives or analogs thereof. According to the practice of the invention, there are provided 9-substituted 1,8-dichloro-anthracene compounds of the Formula III:

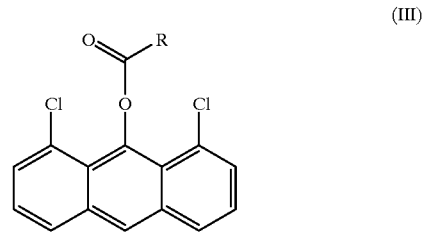

(III)

wherein R represents a straight or branched chain alkyl group having 1–6 carbons and may be substituted with one or more of the groups $R_1$, wherein $R_1$ represents the groups selected from COOH or an ester alky thereof having 1 to 4 carbons, —OH, halogen, $NO_2$, $CH_3O$, $CH_3CH_2O$, phenyl and $CH_3CH_2CH_2O$. Alternatively, R may be phenyl, benzyl, or phenyl or benzyl substituted with one or more groups $R_2$, wherein $R_2$ represents the a group select from a straight or branched chain alkyl group having 1 to 4 carbon atoms, halogen, $NO_2$, $CH_3O$, $CH_3CH_2O$, $CH_3CH_2CH_2O$ and an ester alkyl having an alkyl group of 1 to 4 carbon atoms.

13 Claims, 2 Drawing Sheets

(1a)

(3)

(4)

OTHER PUBLICATIONS

Krapcho, A.P., Synthesis and Antitumor Evaluations of Symmetrically and Unsymmetrically Substituted 1,4–Bis [(aminoalkyl)amino]anthracene–9,10–diones and 1,4–Bis [(aminoalkyl)amino]–5,8–dihydroxyanthracene–9,10–diones;J. Med. Chem., vol. 34, p. 2373–2380 (1991).

Morier–Teissier, Synthesis and Antitumor Properties of an Anthraquinone Bisubstituted by the Copper Chelating Peptide Gly–Gly–L–His; E.; J. Med. Chem., vol. 36, p. 2084–2090 (1993).

Krebs, A., Untersuchungen zur Strukturspezifitat der Psoriasisheilmittel Chrysarobin und Dithrano; Schaltegger, H. Hautarzt, vol. 20, p. 204–209 (1969).

Denny, W.A., DNA–intercalating ligands as anti–cancer drugs: prospects for future design; Anti–Cancer Drug Design, vol. 4, p. 241–263 (1989).

Faulds, D., Mitoxantrone–A Review of its Pharmacodynamic and Pharmacokinetic Properties, and Therapeutic Potential in the Chemotherapy of Cancer; Drugs, vol. 41, p. 400–449 (1991).

Benekli, M.; Mitoxantrone–Induced Bradycardia; Ann. Intern. Med., vol. 126, p. 409 (1997).

Krapcho, A.P., Synthesis and Antitumor Evaluation of 2,5–Disubstituted–Indazolo[4,3–gh] isoquinolin–6(2H)–ones(9–Aza–anthrapyrazoles); J. Med. Chem., vol. 41, p. 5429–5444 (1988).

Moore, H. W., Natural Quinones as Quinonemethide Precursors–ideas in Rational Drug Design; Drugs Expl. Clin. Res., vol. 12, p. 475–494 (1986).

Johnson, R.K., Experimental Antitumor Activity of Aminoanthraquinones; Cancer Treat. Rep., vol. 63, p. 425–439 (1979).

Harley, C.B.; Telomeres shorten during ageing of human fibroblasts; Nature, vol. 345, p. 458–460 (1990).

Philip, J. Perry; 1,4–and 2,6–Disubstituted Amidoanthracene–9,10–dione Derivatives as Inhibitors of Human Telomerase; J. Med. Chem., vol. 41, P. 3253–3260 (1998).

Philip, J.. Perry; Human Telomerase Inhibition by Regioisomeric Disubstituted Amidoanthracene–9,10–diones; J. Med. Chem., vol. 41, p. 4873–4884 (1998).

* cited by examiner (1a)

(3)

(4)

SYNTHESIS OF 1,8-DICHLORO-ANTHRACENE ANALOGUES AND PHARMACEUTICAL COMPOSITIONS BASED THEREON

BACKGROUND OF THE INVENTION

1. Field Of The Invention

This invention relates to novel anthracene compounds useful in the treatment of allergic, inflammatory, and tumor conditions, and to therapeutic compositions containing such compounds. The invention provides therapeutic compositions effective at low doses with low irritancy. The agents of the invention form a distinct class, lacking the anthrone or anthraquinone nucleus.

2. Description Of The Prior Art

Anthracenone derivatives display potent and selective antitumor activity against inter alia GBM and KB cell lines, telomerase inhibition and antioxidant activity, and their mechanism of action, though yet to be defined, may be novel.

The discovery of the antitumor activity of 1,4-bis[(aminoalkyl)amino]anthracene-9,10-diones such as ametantrone (1) and mitoxantrone (2) (see FIG. 1) (Zee-Cheng, R. K. V. et al., *J. Med. Chem*, 21, 291–294, (1978); Zee-Cheng, R. K. V. et al., *J. Pharm. Sci.*, 71, 708–709, (1982); Murdock, K. C. et al., *J. Med. Chem.*, 22, 1024–1030 (1979)) has led to numerous physicochemical and pharmacological studies on the tumoricidal mechanisms of these chemotypes. Krapcho, A. P. et al., *J. Med. Chem.*, 34, 2373–2380, (1991); Morier-Teissier, E. et al., *J. Med. Chem.*, 36, 2084–2090, (1993).

1,8-Dihydroxy-9(10H)-anthracenone (anthralin; dithranol) (3) (see FIG. 1) is recognized as a potent antipsoriatic agent, and has been in clinical use, especially in European countries, for more than half a century. Unna published the first part of his fundamental monograph on the structure-activity relationships of 1,8-dihydroxy-9(10H)-anthracenone and related hydroxyanthrones in 1916. Unna P. G. *Dermatol. Wochenschr.*, 62, 175–183 (1916). 1-Hydroxy-9-anthrone (4) has been shown by Krebs and Schaltegger (Krebs, A.; Schaltegger, H. *Hautarzt*, 20, 204–209, (1969)) to comprise the "minimal basic structure for antipsoriatic activity".

The mechanism of the antitumor activity of the anthracene-9,10-diones such as ametantrone (1) and mitoxantrone (2) is probably multimodal in nature. However, a number of studies have indicated that an intercalative interaction with DNA may be a major cellular event. Denny, W. A. *Anti-Cancer Drug Design*, 4, 241–263 (1989). Mitoxantrone, an anthracene-9,10-dione, has gained an important position in the clinical management of leukemia and lymphomas as well as in combination therapy of advanced breast and ovarian cancers. Faulds, D. et al., *Drugs*, 41, 400–449 (1991). Although mitoxantrone is endowed with an improved tolerance prolife when compared with doxorubicin and other anthracyclines, significant toxic side effects, notably those associated with myelosuppression and cardiotoxicity, remain. Benekli, M. et al., *Ann. Intern. Med.*, 126, 409 (1997).

Mitoxantrone (2) also shows a cross-resistance to cell histotypes developing resistance against doxorubicin mediated by overexpression of glycoprotein. P. Bailly, J. D. et al., *Leukemia*, 11, 1523–1532 (1997). Several studies suggest that intercalation into DNA is a major cellular event and this intercalative interaction may serve as an anchor for the drug at specific base pair sites, which is then followed by the critical cell-killing events. The biochemical basis for the cardiotoxicity exhibited by mitoxantrone is not fully understood. It is generally believed that the in vivo reduction of the quinone moiety is probably more related to the cardiotoxic side effects of mitoxantrone than to its mechanism of cytotoxicity. Krapcho, A. P., et al., *J. Med. Chem.*, 41, 5429–5444 (1998).

Antitumor quinones represent one of the largest classes of clinically approved anticancer agents in the U.S.A., second only to the chloroethyl alkylating agents. Antitumor quinones have been selected from the large number of naturally occurring quinones (Moore, H. W. et al., *Drugs Expl. Clin. Res.*, 12, 475–494, (1986)) and from synthetic quinones (Bruce, J. M. ed., *Benzoquinones and Related Compounds*, Vol. 3, Part 4, 1–306, (1974)). The planar tricyclic system is known to intercalate into DNA base pairs and interfere in the transcription and replication processes of the cell. Johnson, R. K. et al., Cancer Treat. Rep., 63, 425–439, (1979); Lown, J. W. et al., Biochemisty, 24, 4028–4035, (1985). The DNA binding affinity (quantified as a binding affinity constant) and the dissociation rate constant for the DNA-ligand complex have been evaluated. Drug-DNA binding constants for ametantrone (1), mitoxantrone (2) and related congeners with calf thymus DNA show a large sensitivity to the position and number of the OH substitutions and the nature of the charged side chain. Denny, W. A. *Anti-Cancer Drug Design*, 4, 241–263 (1989).

Anthraquinone-based compounds currently occupy a prominent position in cancer chemotherapy, with the naturally occurring aminoglycoside anthracycline doxorubicin and the aminoanthraquinone mitoxantrone both being in clinical use. These and other experimental anthraquinone derivatives are believed to act at the duplex DNA level, probably through the stabilization of a ternary complex with DNA topoisomerase II. Zunino, F. et al., *Anti-Cancer Drug Des.*, 5, 307–317 (1990).

There is increasing evidence that intercalation into DNA represents an attractive target for the rational design of new anticancer agents in view of its central role in the control of cellular proliferation. Normal human cells undergo a finite number of cell divisions and ultimately enter a nondividing state called replicative senescence. During successive rounds of cell division, this end-replication problem results in telomere shortening and ultimately senescence. As such, the loss of telomeric repeats after each round of cell division has been likened to a "biological clock" limiting the proliferative life span of normal somatic cells. Harley, C. B. et al., *Nature*, 345, 458–460 (1990). Consequently, telomerase has been proposed as a potentially highly selective target for the development of a novel class of antiproliferative agents.

Additional references disclose 1,4- and 2,6-disubstituted or regioisomeric amidoanthracene-9,10-dione derivatives as inhibitors of human telomerase include Philip J. Perry et al. *J. Med. Chem.* 41, 3253–3260 (1998) and Philip J. Perry et al. *J. Med. Chem.* 41, 4873–4884 (1998). However, in order for a therapeutic treatment to be effective, both the inflammatory and hyperproliferative aspects of the condition must be addressed without an increase in toxicity or the lack of patient tolerance observed with existing therapeutic agents.

Substantial evidence suggests that free radicals and active oxygen species play a key role in both the therapeutic activity and side effects of anthracenone derivatives. The generation of free radicals from quinones occurs by addition of an electron to the quinone to form semi-quinone free radicals which then transfer an electron to molecular oxygen to afford superoxide radical anion. The resulting radical anions ultimately lead to hydroxyl radicals which can damage cardiac tissue. Despite the attempts to rationalize the cardiotoxicity of anthracene-9,10-dione antitumor agents, few compounds have been shown to possess both good antitumor activity and little or no cardiotoxicity. Consequently there appears to be no way to predict which compounds will be cardiotoxic and which compounds will not. One is thus confronted with the major problem of designing molecules with high efficacy and no toxicity. Krapcho, A. P. et al., *J. Med. Chem.*, 41, 5429–5444 (1998).

As noted above, cancer is typically characterized by hyperproliferative component. There is thus a continuing need for effective compounds that address these aspects of cancer disease.

The present invention differs from the prior art in the absence of the anthrone or anthraquinone structures. This modification is not suggested by the prior art which teaches the significance of the quinone structure in the antitumor activity of these agents through free radical generation.

The invention satisfies the need for effective therapeutic agents for treating allergic, inflammatory and tumor conditions that minimizes or eliminates undesirable allergic or inflammatory effects.

SUMMARY OF THE INVENTION

The present invention is related to 1,8-dichloro-anthracene compounds and analogues thereof, the structure of which is based on the tricyclic ring of anthraquinones. The compounds according to the invention are esters synthesized by the reaction of an acid chloride with 1,8-dichloro-9(10H)-anthracenone and show enhanced antiproliferative activity. However, during their preparation, the characteristic quinone structure is destroyed. These blocked compounds may be further modified by introducing an arylacyl or alkylacyl substituent. The novel 1,8-dichloro-anthracene compounds and analogues thereof have therapeutic utility with respect to allergic, inflammatory or tumor conditions.

Accordingly, in one embodiment of the invention, there is provided an anthracene compound according to Formula I, as defined below, said compound containing a substituent R, wherein R represents a branched or straight chain alkyl group having from 1 to 6 carbon atoms, or a phenyl or benzyl group that may be substituted with at least one substituent selected from the group consisting of a short chain alkyl, carboxyl, carboxyl ester, hydroxy, halogen, nitro, alkoxy, phenyl, benzyl, substituted benzyl and substituted phenyl groups.

In a preferred embodiment of the invention, R represents a substituted phenyl group having at least one substituent selected from the group consisting of methyl, halogen, methoxy and nitro groups.

In another preferred embodiment, R represents a straight or branched chain alkyl group having 1 to 4 carbon atoms, which may be substituted with a group selected from acyl and phenyl groups. Additionally, there are provided compounds which are functional analogs of the compound of Formula III.

The invention further provides therapeutic compositions comprising a therapeutically effective amount of at least one compound of the invention and a pharmaceutically acceptable carrier. These compositions of the invention have antiproliferative effects and antineoplastic effects.

Further additional representative and preferred aspects of the invention are described below according to the following detailed description of the invention. The above objectives and advantages of the invention are illustrative, and not exhaustive, of those which can be achieved by the invention. The examples presented herein are non-limiting. Thus, these and other objectives and advantages of the invention will be apparent from the description herein, both as embodied herein and as modified in view of any variations which will be apparent to those skilled in the art.

DETAILED DESCRIPTION OF THE INVENTION

The contents of all patents, patent applications, published articles, books, reference manuals and abstracts cited herein are hereby incorporated by reference in their entirety to more fully describe the state of the art to which the invention pertains.

The compounds of the invention are 1,8-dichloro-anthracene analogs. According to the invention, there are provided esterified 1,8-dichloro-anthracene compounds according to Formula III.

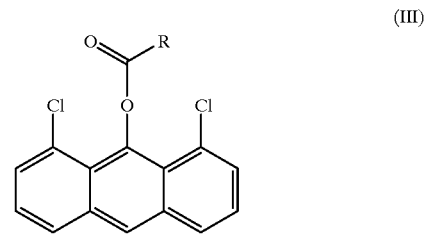

(III)

wherein R represents a straight or branched chain alkyl group, preferably having 1 to 6 carbon atoms, which may be substituted with one or more of the groups $R_1$, wherein $R_1$ represents a group selected from halogen, $NO_2$, $CH_3O$, $CH_3CH_2O$, $CH_3CH_2CH_2O$ and phenyl R may also be a phenyl or benzyl group, which may be substituted with one or more of the phenyl groups $R_2$, wherein $R_2$ represents a group selected from a straight or branched chain alkyl group having 1 to 4 carbon atoms, halogen, $NO_2$, $CH_3O$, $CH_3CH_2O$, $CH_3CH_2CH_2O$.

In preferred embodiments of the invention, R represents a straight or branched alkyl chain having 1 to 4 carbon atoms which may be substituted with groups $R_1$, wherein $R_1$ represents a group selected from Cl, $NO_2$, and $CH_3O$. In another preferred embodiment, R is benzyl which may be substituted with one or more groups $R_2$, wherein $R_2$ presents a group selected from a straight or branched chain alkyl group having 1 to 4 carbon atoms, Cl, $NO_2$, and $CH_3O$. Preferred compounds of the invention are described in Table 1, infra.

Figure 1:
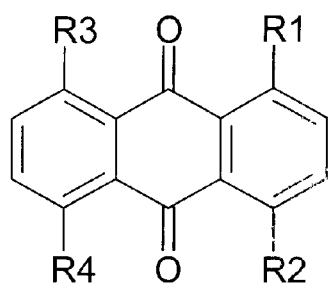
FIG. 1 is a drawing showing the structure of existing therapeutic anthraquinonic derivatives. Ametantrone (1) and mitoxantrone (2) have the same general formula (1a); in ametantrone the substitutes have the following definitions:
(1) $R_3=R_4=H$; $R_1=R_2=$—NH—$(CH_2)_2$—NH—$(CH_2)_2$—OH; and, in mitoxantrone, the following:
(2) $R_3=R_4=OH$; $R_1=R_2=$—NH—$(CH_2)_2$—NH—$(CH_2)_2$—OH anthralin (3) and 1hydroxy-9-anthrone (4) exhibit the structural formula of (3) and (4) respectively.
Figure 1:
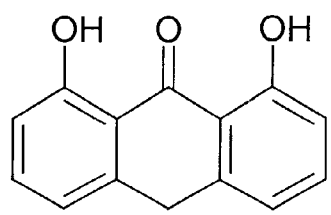
Figure 1:
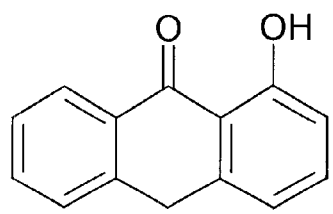
Figure 2:
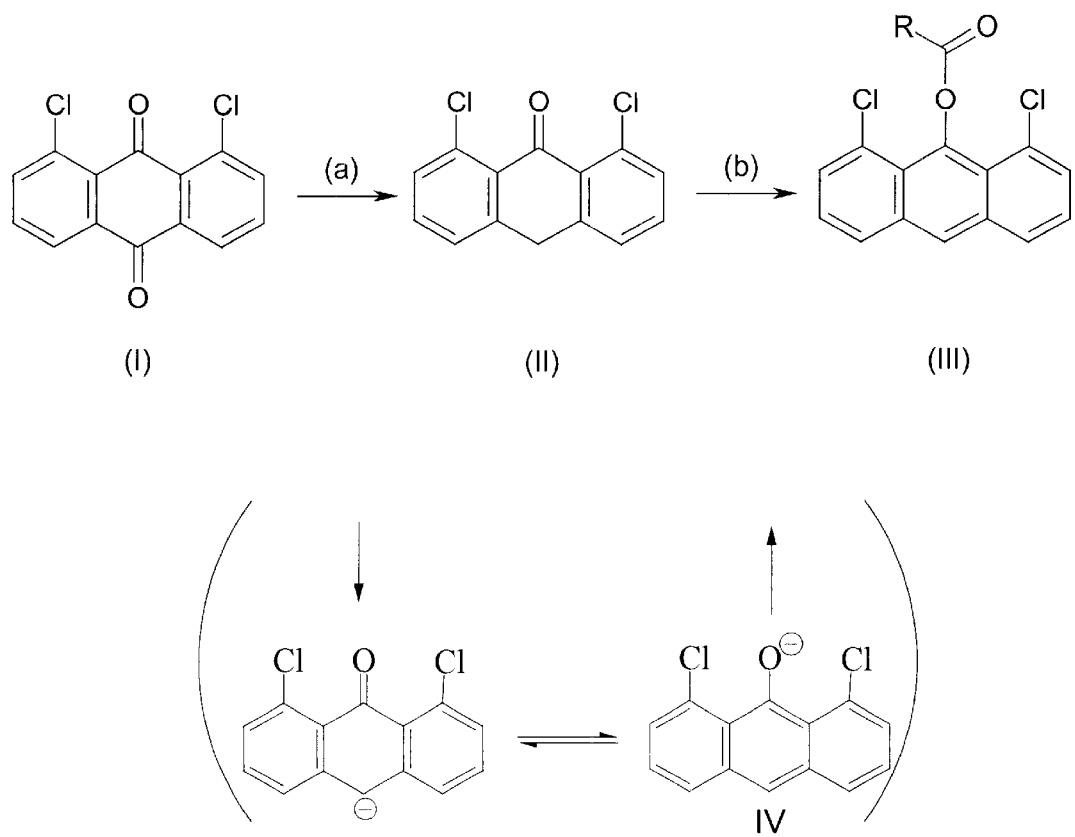
FIG. 2 is a schematic drawing of the general synthetic method used to prepare the novel 1,8-dichloro-anthracene compounds of the inventions. The synthesis reagents include: (a) $SnCl_2$, HCl, HOAc, 118° C.; and (b) RCOCl, pyridine, $CH_2Cl_2$.

In the course of synthesis of the 1,8-dichloro-anthracenes, it was found that the molecule reacted with acid chloride reagents in an unusual manner. Introduction of the 9-ester functionality onto the anthracene nucleus (compounds 3a–w) was achieved by reaction of the appropriate acylchlorides with 1,8-dichloro-9(10H)-anthracenone under weakly basic conditions, for example in the presence of pyridine, under anhydrous inert conditions, reaction occurs at ambient temperatures and up to the reflux temperature of the solvent employed. Esterification takes place at the C-9 oxygen position, most likely through the enol tautomer, (IV) (FIG. 2). The acylchlorides which are used in the syntheses include those of the formula RCOCl wherein R represents a straight or branched chain alkyl group, preferably having 1 to 6 carbon atoms, which may be substituted with one or more of the group selected from halogen, $NO_2$, $CH_3O$, $CH_3CH_2O$, $CH_3CH_2CH_2O$ and phenyl. R may also be a phenyl or benzyl group, which may be substituted with one or more of the groups $R_2$, wherein $R_2$ represents a group selected from a straight or branched chain alkyl group having 1 to 4 carbon atoms, halogen, $NO_2$, $CH_3O$, $CH_3CH_2O$, $CH_3CH_2CH_2O$.

Many of the improved anthracene compounds provided according to the invention are effective at low dosages for treatment of patients suffering from allergic, inflammatory or tumor conditions. Because these compounds may be administered at low concentrations, the undesirable allergic, irritancy or inflammatory effects normally associated with anthraquinone and related compounds are substantially eliminated. These effects may be caused by free radicals or active oxygen species generated by the anthraquinone compounds.

For the pharmaceutical compositions of the invention, a preferred embodiment utilizes salts of 1,8-dichloroanthracene compounds with a pharmaceutically acceptable base. Excipients can be added to the preparation of 1,8-dichloroanthracene derivatives of the present invention, such as magnesium stearate, corn starch, starch, lactose, sodium hydroxymethylcellulose, ethanol, glycerol etc. for tablet, pill or other solid preparations. The pH value of other forms of administration, e.g. injection, may be adjusted with phosphate buffer. Generally, the dose used for injection is from about 25 mg to about 100 mg. Oral preparations general utilize a dose of about 3 mg to about 500 mg administered 2 to 3 times daily.

Clinical Indications Subject to Treatment

The following conditions are representative of inflammatory, allergic, antioxidant, or neoplastic conditions that are suitable for treatment according to the practice of the invention and are non-limiting. Each of these conditions involves intimation hyperproliferation and/or generation of free radicals and active oxygen species. Conditions treatable according to the invention are not limited to the representative conditions illustrated below.

Neoplastic Conditions

The therapeutic compositions of the invention may be used in the treatment of a wide variety of cancers such as carcinomas, sarcomas, melanomas and lymphomas, which may affect a wide variety of organs, including, for example, the lungs, mammary tissue, prostate gland, small or large intestine, liver, heart, skin, pancreas and brain. The therapeutic compositions may be administered in the case of treatment of tumors, for example, by injection (intravenously, intralesionally, peritoneally, subcutaneously), or by topical application and the like as would be suggested according to the routine practice of the art.

Psoriasis and Contact Dermatitis

Psoriasis is a widespread, chronic, inflammatory and scaling skin disease. Contact dermatitis, in contrast, is a short term allergic condition characterized by scaling skin. Both psoriasis and contact dermatitis are characterized by increased epidermal cell proliferation at the affected site or sites, i.e. lesion(s). Müller, K., Huang, H.-S. and Wiegrebe, W., *J. Med. Chem.*, 39, 3132–3138 (1996).

Arthritic Disease

Rheumatoid arthritis is a chronic inflammatory disease primarily of the joints that may result in permanent loss of joint function. Irreversible loss of joint function is attributed to severe degradation of collagen, bone, ligament and tendon. Associated chronic inflammation results, in part, from immune response at the affected joint, although the exact nature of the triggering antigens is unknown. The immune response may be autoimmune in origin. Mullins, D. E. and Rohrlich, S. T. *Biochemica et Biophysica Acta*, 695, 177–214 (1983) at 192–193 described the etiology of the disease in detail. Briefly, there is a progressive loss of cartilage (a connective tissue) caused by invading cells. Both collagen and proteoglycan components of the cartilage are degraded by enzymes released at the affected site.

Therapeutic Compositions and Administration Thereof

The amount of novel 1,8-dichloroanthracene compound or analogues thereof according to the invention administered to a patient for the prevention or inhibition of an inflammatory or allergic condition, or for antiproliferative or antineoplastic effect, can be determined readily for any particular patient according to recognized procedures. Additional information useful in the selection of therapeutic compositions is provided as follows: For use in the treatment of inflammatory or degenerative conditions, as those terms are recognized in the art, the therapeutic compositions may be administered, for example, by injection at the affected site, by aerosol inhalation (as in the case of emphysema or pneumonia), or by topical application or transdermal absorption as would also be suggested according to the routine practice of the art.

As described above, 1,8-dichloro-anthracene compounds of the invention may be incorporated into a pharmaceutically acceptable carrier or carriers for application (directly or indirectly) to the affected area. The nature of the carrier may vary widely and will depend on the intended location of application and other factors well known in the art. The carriers may be comparable to those used with anthralin or anthracenone compounds, which are well known in the art. See, for example, Kammerau, B. et al., *J. Investigative Dermatology*, 64, 145–149 (1975).

Preparation of the Compounds of Invention

Novel 1,8-dichloroanthracenes according to Formula III may be prepared according to FIG. 2. Reduction of 1,8-dichloroanthraquinone (I) with $SnCl_2$ in boiling HCl and acetic acid proceeds with concomitant ether cleavage and leads to the corresponding 1,8-dichloro-9(10H)-anthracenone (II). Introduction of the 9-ester functionality onto the anthrone nucleus (compounds 3a–w) was achieved by reaction of the appropriate acyl chlorides with 1,8-dichloro-9(10H)-anthracenone under weakly basic conditions (pyridine). In the course of synthesis of the 1,8-dichloroanthracene compounds of the invention, it was found that the molecule reacted with acid chlorides in an unusual manner. During the reaction, esterification takes place at the C-9 oxygen, presumably via the enol tautomer IV (FIG. 2). When the anthracene was allowed to react with acyl chlorides in $CH_2Cl_2$ with catalytic amounts of pyridine, the reaction time was reduced as compared to the noncatalyzed reaction. Specific methods for the preparation of several compounds according to the present invention are described below in Example 1 and the structure of each of the synthesized compounds is confirmed by $^1$H-NMR spectrometry, mass spectrometry and elementary analysis as shown in Example 2.

EXAMPLES

The following non-limiting examples are representative of the practice of the invention.

Example 1
Methods of Synthesis

There are hereafter provided processes by which the novel 1,8-dichloro-anthracene compounds described in Table 1 were produced. Such procedures, and procedures adapted therefrom will allow one skilled in the art to prepare other compounds in accordance with the invention. However, the invention is not limited to compounds prepared by the method described. The compounds may be made by existing reactions or other methods which may not be presently known.

A general procedure for the synthesis of the 9-substituted 1,8-dichloroanthracene compounds of the invention follows. Reduction of 1,8-dichloroanthraquinone (I) with $SnCl_2$ in boiling HCl and acetic acid proceeds with concomitant ether cleavage and leads to the corresponding 1,8-dichloro-9 (10H)-anthracenone (II). To a solution of 1,8-dichloro-9 (10H)-anthracenone (1 mmol) and 0.1 mL of pyridine in dry $CH_2Cl_2$ (20 mL) was added dropwise to a solution of an appropriate acyl chloride (3 mmol) in dry $CH_2Cl_2$ (10 mL) under $N_2$. The reaction mixture was stirred at room temperature or refluxed for several hours. The solvent was removed and the residue purified by recrystallization and chromatography. This procedure was used to synthesize each of the compounds in Table 1.

All temperatures are provided in degrees centigrade. Melting points reported in Table 1 were determined with a Büchi 530 melting point apparatus and are uncorrected. Chromatography refers to column chromatography using silica gel (E. Merck, 70–230 mesh). $^1$H-NMR spectra were recorded with a Varian GEMINI-300 (300 MHz); δ values are in ppm relative to a tetramethylsilane internal standard. Fourier transform IR spectra (KBr) were recorded on a Perkin-Elmer 983G spectrometer. Mass spectra (MS) (EI, 70 eV), were obtained on a Finnigan MAT TSQ-46 or Finnigan MAT TSQ-700. UV spectra were recorded on a Shimadzu UV-160.

Example 2
Structural Confirmation (1)1,8-Dichloro-9-acetoxyanthracene (3a)

The compound was synthesized as in Example 1 and analyzed by $^1$H-NMR: (500 MHz, $CDCl_3$) δ9.23 (H, s, H-10), 7.87–7.85 (2H, m, H-2,7), 7.64 (2H, t, J=8.0, H-4,5), 7.45–7.42 (2H, m, H-3,6), 2.62 (3H, s, $COCH_3$); MS m/z 304 (15), 262 (100), 227 (44); Anal. ($C_{16}H_{10}O_2Cl_2$); C, H.

(2)1,8-Dichloro-9-bromoacetoxyanthracene (3b)

The compound was synthesized as in Example 1 and analyzed by $^1$H-NMR: (500 MHz, $CDCl_3$) δ9.24 (H, s, H-10), 7.90 (2H, d, H-2,7), 7.63 (2H, d, H-4,5), 7.45–7.42 (2H, m H-3,6) 4.31 (3H, s, $CH_2$); MS m/z 384 (15), 262 (100), 227 (34); Anal. ($C_{16}H_9O_2Cl_2Br$); C, H.

(3)1,8-Dichloro-9-chloroacetoxyanthracene (3c)

The compound was synthesized as in Example 1 and analyzed by $^1$H-NMR: (500 MHz, $CDCl_3$) δ9.25 (H, s, H-10), 7.84 (2H, d, H-2,7), 7.64 (2H, d, H-4,5), 7.45–7.42 (2H, m H-3,6) 4.58 (3H, s, $CH_2$); MS m/z 339 (20), 262 (100), 227 (33); Anal. ($C_{16}H_9O_2Cl_3$); C, H.

(4)1,8-Dichloro-9-propionoxyanthracene (3d)

The compound was synthesized as in Example 1 and analyzed by $^1$H-NMR: (500 MHz, $CDCl_3$) δ9.22 (H, s, H-10), 7.85–7.83 (2H, dd, H-2,7), 7.63 (2H, d, H-4,5), 7.4–7.41 (2H, dd, H-3,6), 2.98–2.93 (2H, q, $CH_2$), 1.48–1.45 (3H, t, $CH_3$); MS m/z 319 (13), 262 (100), 227 (33); Anal. ($C_{17}H_{12}O_2Cl_2$); C, H.

(5)1,8-Dichloro-9-isobutyroxyanthracene (3e)

The compound was synthesized as in Example 1 and analyzed by $^1$H-NMR: (500 MHz, $CDCl_3$) δ9.20 (H, s, H-10), 7.80 (2H, d, H-2,7), 7.61 (2H, d, H-4,5), 7.41 (2H, t, H-3,6) 3.20–3.15 (H, m, CH), 1.56–1.47 (6H, m, 2×$CH_3$); MS m/z 333 (12), 262 (100), 227 (30); Anal. ($C_{18}H_{14}O_2Cl_2$); C, H.

(6)1,8-Dichloro-9-(2-chlorpropionoxy)anthracene (3f)

The compound was synthesized as in Example 1 and analyzed by 1H-NNR: (500 MHz, $CDCl_3$) δ9.20 (H, s, H-10), 7.88 (2H, d, H-2,7), 7.64 (2H, dd, H-4,5), 7.44 (2H, dd, H-3,6), 4.96–4.91 (H, q, CH), 2.02 (3H, q, $CH_3$); MS m/z 353 (19), 262 (100), 227 (28); Anal. ($C_{17}H_{11}O_2Cl_3$); C, H.

(7)1,8-Dichloro-9-dichloracetoxyanthracene (3g)

The compound was synthesized as in Example 1 and analyzed by $^1$H-NMR: (500 MHz, $CDCl_3$) δ9.32 (H, s, H-10), 7.95 (2H, t, H-2,7), 7.69 (2H, d, H-4,5), 7.53–7.48 (2H, m, H-3,6) 6.45 (H, s, CH); MS m/z 374 (30), 261 (100), 227 (25); Anal. ($C_{16}H_8O_2Cl_4$); C, H.

(8)1,8-Dichloro-9-butyroxyanthracene (3h)

The compound was synthesized as in Example 1 and analyzed by $^1$H-NMR: (500 MHz, $CDCl_3$) δ9.21 (H, s, H-10), 7.83 (2H, d, H-2,7), 7.62 (2H, d, H-4,5), 7.43–7.39 (2H, dd, H-3,6), 2.90–2.87 (2H, t, $CH_2$), 2.01–1.94 (2H, m, $CH_2$), 1.18–1.15 (2H, t, $CH_3$); MS m/z 333 (15), 262 (100), 227 (28); Anal. ($C_{18}H_{14}O_2Cl_2$); C, H.

(9)1,8-Dichloro-9-(4-bromobutyroxy)anthracene (3i)

The compound was synthesized as in Example 1 and analyzed by $^1$H-NMR: (500 MHz, $CDCl_3$) δ9.25 (H, s, H-10), 7.86 (2H, d, J=8.8 Hz, H-2,7), 7.66 (2H, d, J=6.6 Hz, H-4,5), 7.47 (2H, t, J=7 Hz, H-3,6), 3.65 (2H, t, $CH_2$), 3.19 (2H, t, $CH_2$), 2.45 (2H, m, $CH_2$); MS m/z 412 (5) 262 (100), 227 (30); Anal. ($C_{18}H_{13}BrO_2Cl_2$); C, H.

(10)1,8-Dichloro-9-(4-chlorbutyroxy)anthracene (3j)

The compound was synthesized as in Example 1 and analyzed by $^1$H-NMR: (500 MHz, $CDCl_3$) δ9.22 (H, s, H-10), 7.83–7.81 (2H, m, H-2,7), 7.63–7.62 (2H, m, H-4,5) 7.44–7.41 (2H, m, H-3,6), 3.77–3.75 (2H, m, $CH_2$), 3.15 (2H, t, $CH_2$), 2.38–2.32 (2H, m, $CH_2$); MS m/z 367 (8) 262 (100), 227 (29); Anal. ($C_{18}H_{13}O_2Cl_3$); C, H.

(11)1,8-Dichloro-9-hexanoyloxyanthracene (3k)

The compound was synthesized as in Example 1 and analyzed by $^1$H-NMR: (500 MHz, $CDCl_3$) δ9.21 (H, s, H-10), 7.83 (2H, d, H-2,7), 7.63 (2H, d, H-4,5), 7.42 (2H, t, H-3,6), 290 (2H, t, $CH_2$), 1.97–1.91 (2H, m, $CH_2$), 1.55–1.41 (2H, m, $CH_2CH_2$), 0.98–0.96 (3H, t, $CH_3$); MS m/z 361 (10), 262 (100), 227 (29); Anal. ($C_{20}H_{18}O_2Cl_2$); C, H.

(12) 1,8-Dichloro-9-benzoyloxyanthracene (3L)

The compound was synthesized as in Example 1 and analyzed by $^1$H-NMR: (500 MHz, $CDCl_3$) δ9.26 (H, s, H-10), 8.43–8.41 (2H, m, H-2,7), 7.91–7.89 (2H, m, H-4,5), 7.76–7.73 (H, m, H-4'), 7.63–7.60 (4H, m, H-2',3',5',6'), 7.40–7.37 (2H, m, H-3,6); MS m/z 367 (10), 262 (20) 105 (100); Anal. ($C_{21}H_{12}O_2Cl_2$); C, H.

(13) 1,8-Dichloro-9-(o-toluoyloxy)anthracene (3m)

The compound was synthesized as in Example 1 and analyzed by $^1$H-NMR: (500 MHz, $CDCl_3$) δ9.25 (H, s, H-10), 8.58–8.56 (2H, m, H-2,7), 7.94–7.92 (2H, m, H-4,5), 7.64–7.59 (H, m, H-3,6), 7.45–7.38 (4H, m, H-2',3',4',6'), 2.70 (3H, s, $CH_3$); MS m/z 381 (10), 262 (100), 105 (30); Anal. ($C_{22}H_{14}O_2Cl_2$); C, H.

(14) 1,8-Dichloro-9-(m-toluoyloxy)anthracene (3n)

The compound was synthesized as in Example 1 and analyzed by $^1$H-NMR: (500 MHz, $CDCl_3$) δ9.26 (H, s, H-10), 8.23–8.22 (2H, m, H-2,7), 7.91 (2H, d, J=8.5 Hz, H-4,5), 7.63 (2H, d, J=8.5 Hz, H-3,6), 7.56–7.37 (4H, m, H-2',4',5',6'), 2.50 (3H, s, $CH_3$); MS m/z 381 (42), 261 (40), 119 (100); Anal. ($C_{22}H_{14}O_2Cl_2$); C, H.

(15) 1,8-Dichloro-9-(p-toluoyloxy)anthracene (3o)

The compound was synthesized as in Example 1 and analyzed by $^1$H-NMR (500 MHz, $CDCl_3$) δ9.26 (H, s, H-10), 8.31–8.29 (2H, m, H-2,7), 7.92–7.90 (2H, m, H-4,5), 7.64–7.62 (2H, m, H-3,6), 7.42–7.36 (4H, m, H-2',3',5',6'), 2.51 (3H, s, $CH_3$); MS m/z 381 (12), 262 (10), 119 (100); Anal. ($C_{22}H_{14}O_2Cl_2$); C, H.

(16) 1,8-Dichloro-9-(3-chlorbenzoyloxy)anthracene (3p)

The compound was synthesized as in Example 1 and analyzed by $^1$H-NMR (500 MHz, $CDCl_3$) δ9.28 (H, s, H-10), 8.31–8.29 (2H, m, H-2,7), 7.92–7.90 (2H, m, H-4,5), 7.64–7.62 (2H, m, H-3,6), 7.42–7.36 (4H, m, H-2',3',5',6'), 2.51 (3H, s, $CH_3$); MS m/z 381 (12), 262 (10), 119 (100); Anal. ($C_{22}H_{14}O_2Cl_2$); C, H.

Example 3

Growth Inhibition Assay

Growth inhibition was measured in three human carcinoma cell lines using in vivo assay as described previously. Hwang, J.-M. et al., *Chin. Med. J.* (Taipei), 51, 166–175 (1993). Human oral epidermoid carcinoma cells (KB cell line), human cervical carcinoma cells of ME 180 (GBM8401) and Chinese hamster ovary (CHO) cells grown in plateau phase were used in all experiments. Each cell line was further divided into control and experimental groups. Stock solutions of the test compounds were prepared in DMSO and diluted with DMEM to give a final concentration in DMSO of 0.2%. Controls were performed with DMSO or with medium alone. Forty-eight hours after addition of the test compound to the culture, the medium was removed and each well was rinsed with 100 μL PBS. The cells were then incubated with sterile 0.5% trypsin, 0.2% EDTA in PBS for 20 minutes at 37° C. The detached cells from each well were suspended in DMEM and dispersed into single cells by gentle pipetting through an Eppendorf pipette and cell growth was determined directly by counting the cells in a Neubauer counting chamber using phase contrast microscopy. Inhibition was calculated by comparison of the mean values of the test compound (N=3) with the control (N=6–8) activity: (1-test compound/control)×100.

Inhibition was found to be statistically significant compared to that of control (Student's t-test; P=0.05). $IC_{50}$ values (concentration required to inhibit cell growth by 50%) were determined for each agent which was derived by interpolation of a log inhibitor concentration versus response plot using four or more different concentrations of the compound spanning the 50% inhibition point. Several compounds of the invention had an antiproliferative $IC_{50}$ value of less than 1.1 μM for GBM cell line.

Example 4

Lipid Peroxidation Assay

Rat brain homogenate was prepared from the brains of freshly killed Wistar rats and its peroxidation in the presence of iron ions was measured by the thiobarbituric acid (TBA) method, as described by Teng, C. M. et al., *Eur. J. Pharmacol.*, 303, 129–139 (1996). Tetramethoxy-propane was used as a standard, and the results were expressed as nanomoles of malondialdehyde equivalents per milligram of protein of rat brain homogenates.

In brief, whole brain tissue, excluding the cerebellum, was washed and homogenized in 10 volumes of ice-cold Krebs buffer (10 mM N-2-hydroxyethylpiperazine-N'-2-ethanesulfonic acid (Hepes), 10 mM glucose, 140 mM NaCl, 3.6 mM KCl, 1.5 mM $CaCl_2$, 1.4 mM $KH_2PO_4$, 0.7 mM $MgSO_4$, pH 7.4) using a glass Dounce homogenizer. The homogenate was centrifuged at low speed (1000×g) for 10 min, and the resulting supernatant (adjusted to 2 mg/mL) was used immediately in lipid peroxidation assays.

The reaction mixture with test compounds or vehicle was incubated for 10 min, then stimulated by addition of ferrous ion (200 μM, freshly prepared), and maintained at 37° C. for 30 min. The reactions were terminated by adding 10 μL of ice-cold trichloroacetic acid solution (4% (w/v) in 0.3 N HCl) and 200 μL of thiobarbituric acid-reactive substance reagent (0.5% (w/v) thiobarbituric acid in 50% (v/v) acetic acid). After boiling for 15 minutes, the samples were cooled and extracted with 1-butanol. The extent of lipid peroxidation was estimated as thiobarbituric acid-reactive substances and was read at 532 run in a spectrophotometer (Shimadzu UV-160).

The embodiments and non-limiting examples illustrated and discussed in this specification are intended only to teach those skilled in the art the best way known to the inventors to make and use the invention. Nothing in this specification should be considered as limiting the scope of the present invention.

TABLE 1

Preferred Novel 1,8-Dichloro-Anthracene Compounds

| Comp'd No. | R group | Formula | MW | mp (° C.) |
|---|---|---|---|---|
| 3a | $CH_3$ | $C_{16}H_{10}O_2Cl_2$ | 305.16 | 130–131 |
| 3b | $CH_2Br$ | $C_{16}H_9O_2Cl_2Br$ | 384.06 | 192–193 |
| 3c | $CH_2Cl$ | $C_{16}H_9O_2Cl_3$ | 339.60 | 178–180 |
| 3d | $CH_2CH_3$ | $C_{17}H_{12}O_2Cl_2$ | 319.18 | 150–152 |
| 3e | $CH(CH_3)_2$ | $C_{18}H_{14}O_2Cl_2$ | 332.17 | 184–186 |
| 3f | $CH(CH_3)Cl$ | $C_{17}H_{11}O_2Cl_3$ | 353.63 | 172–174 |
| 3g | $CHCl_2$ | $C_{16}H_8O_2Cl_4$ | 374.05 | 178–180 |

TABLE 1-continued

Preferred Novel 1,8-Dichloro-Anthracene Compounds

| Comp'd No. | R group | Formula | MW | mp (° C.) |
|---|---|---|---|---|
| 3h | (CH$_2$)$_2$CH$_3$ | C$_{18}$H$_{14}$O$_2$Cl$_2$ | 333.21 | 152–154 |
| 3I | (CH$_2$)$_3$Br | C$_{18}$H$_{13}$O$_2$BrCl$_2$ | 412.11 | 155–157 |
| 3j | (CH$_2$)$_3$Cl | C$_{18}$H$_{13}$O$_2$Cl$_3$ | 367.65 | 154–156 |
| 3k | (CH$_2$)$_4$CH$_3$ | C$_{20}$H$_{18}$O$_2$Cl$_2$ | 361.26 | 136–138 |
| 3L | C$_6$H$_5$ | C$_{21}$H$_{12}$O$_2$Cl$_2$ | 367.23 | 183–185 |
| 3m | 2-CH$_3$C$_6$H$_4$ | C$_{22}$H$_{14}$O$_2$Cl$_2$ | 381.26 | 168–170 |
| 3n | 3-CH$_3$C$_6$H$_4$ | C$_{22}$H$_{14}$O$_2$Cl$_2$ | 381.26 | 196–198 |
| 3o | 4-CH$_3$C$_6$H$_4$ | C$_{22}$H$_{14}$O$_2$Cl$_2$ | 381.26 | 220–222 |
| 3p | 3-ClC$_6$H$_4$ | C$_{21}$H$_{11}$O$_2$Cl$_3$ | 401.67 | 174–175 |
| 3q | 4-ClC$_6$H$_4$ | C$_{21}$H$_{11}$O$_2$Cl$_3$ | 401.67 | 178–180 |
| 3r | 4-NO$_2$C$_6$H$_4$ | C$_{21}$H$_{11}$NO$_4$Cl$_2$ | 412.22 | 230–231 |
| 3s | 3-NO$_2$C$_6$H$_4$ | C$_{21}$H$_{11}$NO$_4$Cl$_2$ | 412.22 | 170–172 |
| 3t | 2,4-Cl$_2$C$_6$H$_3$ | C$_{22}$H$_{10}$O$_2$Cl$_4$ | 436.12 | 214–215 |
| 3u | CH$_2$CH$_2$C$_6$H$_5$ | C$_{23}$H$_{16}$O$_2$Cl$_2$ | 395.28 | 143–145 |
| | Doxorubicin | | | |
| | Mitomycin-C | | | |
| | Methotrexate | | | |

What is claimed is:

1. A compound having the structure of Formula III:

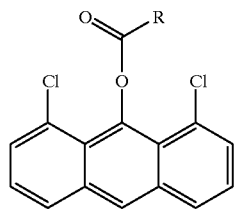

(III)

wherein R represents a straight chain alkyl group having 1 to 6 carbons which is substituted with at least one R$_1$ groups, a branched chain alkyl group having 3 to 6 carbons which is optionally substituted with one or more R$_1$ groups, or a phenyl or a benzyl group which is optionally substituted with one or more R$_2$ groups;

wherein R$_1$ is one selected from the group consisting of halogen, —NO$_2$, —OCH$_3$, —OCH$_2$CH$_3$, —OCH$_2$CH$_2$CH$_3$ and phenyl; and wherein R$_2$ is one selected from the group consisting of a straight chain alkyl group having 1 to 4 carbons, a branched chain alkyl group having 1 to 4 carbons, a halogen, —NO$_2$, —OCH$_3$, —OCH$_2$CH$_3$, and —OCH$_2$CH$_2$CH$_3$.

2. A compound having the structure of Formula III:

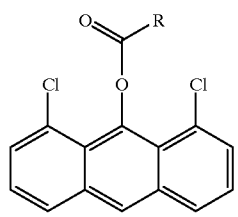

(III)

wherein R represents a benzyl group, or a substituted phenyl or benzyl group having at least one substituent selected from the group consisting of methyl, ethyl, —NO$_2$, —OCH$_3$, and —Cl.

3. A compound having the structure of Formula III,

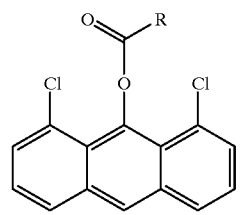

(III)

wherein R represents phenyl or a substituted phenyl group selected from the group consisting of 2-CH$_3$C$_6$H$_4$, 3-CH$_3$C$_6$H$_4$, 4-CH$_3$C$_6$H$_4$, 3-ClC$_6$H$_4$, 3-NO$_2$C$_6$H$_4$, 4-NO$_2$C$_6$H$_4$, 4-Cl, 2-CH$_3$OC$_6$H$_3$, and 2,4-Cl$_2$C$_6$H$_3$.

4. A method for inhibiting or treating an allergic or inflammatory condition comprising administering a therapeutically effective amount of a compound having the structure of Formula III:

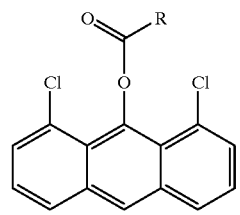

(III)

or a pharmaceutically acceptable salt of said compound and optionally a pharmaceutical carrier to a patient in need of such treatment;

wherein R represents a straight chain alkyl group having 1 to 6 carbons which is optionally substituted with one or more R$_1$ groups, a branched chain alkyl group having 3 to 6 carbons which is optionally substituted with one or more R$_1$ groups, or a phenyl or benzyl which is optionally substituted with one or more R$_2$ groups;

wherein R$_1$ is one selected from the group consisting of halogen, —NO$_2$, —OCH$_3$, —OCH$_2$CH$_3$, —OCH$_2$CH$_2$CH$_3$ and phenyl; and wherein R$_2$ is one selected from the group consisting of a straight chain alkyl group having 1 to 4 carbons, a branched chain alkyl group having 1 to 4 carbons, a halogen, —NO$_2$, —OCH$_3$, —OCH$_2$CH$_3$, and —OCH$_2$CH$_2$CH$_3$.

5. A method for anti-cancer treatment comprising administering a therapeutically effective amount of said compound having the structure of Formula III according to claim 4 or a pharmaceutically acceptable salt of said compound and optionally a pharmaceutical carrier to a patient in need of such treatment.

6. A method for treating abnormal proliferation comprising administering a therapeutically effective amount of said compound having the structure of Formula III according to claim 4 or a pharmaceutically acceptable salt of said compound and optionally a pharmaceutical carrier to a patient in need of such treatment.

7. A method for enhancing an anti-oxidation affect comprising administering a therapeutically effective amount of said compound having the structure of Formula III according to claim 4 or a pharmaceutically acceptable salt of said compound and optionally a pharmaceutical carrier to a patient in need of such treatment.

8. An anti-cancer drug comprising, as an active ingredient, the compound having the structure of Formula III of claim 4.

9. An anti-inflammatory drug comprising, as an active ingredient, the compound having the structure of Formula III of claim 4.

10. An antioxidant comprising, as an active ingredient, the compound having the structure of Formula III of claim 4.

11. An anti-dermatitis cancer drug comprising, as an active ingredient, the compound having the structure of Formula III of claim 4.

12. A method for synthesizing 9-substituted-1,8-dichloroanthrecene derivatives according to claim 1 comprising:

reacting 1,8-dichloroanthracenone with an acylchloride derivative having the formula of RCOCl under weakly basic conditions to give a 9-acyloxy-1,8-dichloroanthracene according to Formula III:

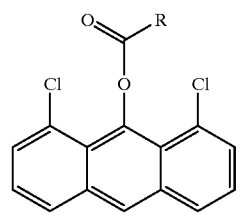

(III)

wherein R is one selected from the group consisting of a straight chain alkyl group having 1 to 6 carbon atoms which is substituted by one or more $R_1$ groups, a branched chain alkyl group having 3 to 6 carbon atoms which is optionally substituted by one or more $R_1$ groups, a phenyl or benzyl group which is optionally substituted by one or more $R_2$ groups, wherein $R_1$ is one selected from the group consisting of a halogen, $-NO_2$, $-OCH_3$, $-OCH_2CH_3$, $-OCH_2CH_2CH_3$, and a phenyl; and wherein $R_2$ is selected from the group consisting of a straight chain alkyl group having 1 to 4 carbon atoms, a branched chain alkyl group having 1 to 4 carbon atoms, a halogen, $-NO_2$, $-OCH_3$, $-OCH_2CH_3$, and $-OCH_2CH_2CH_3$.

13. The method of claim 12, wherein the weakly basic condition is provided by the addition of pyridine.

* * * * *